(12) United States Patent
Kuan

(10) Patent No.: US 7,381,199 B2
(45) Date of Patent: Jun. 3, 2008

(54) STRUCTURE OF SAFETY HYPODERMIC SYRINGE

(76) Inventor: Kuo-Lung Kuan, No. 3-31, Changsheng Lane, Jenmei Li, Peitun Dist., Taichung City (TW)

( * ) Notice: Subject to any disclaimer, the term of this patent is extended or adjusted under 35 U.S.C. 154(b) by 759 days.

(21) Appl. No.: 10/983,631

(22) Filed: Nov. 9, 2004

(65) Prior Publication Data

US 2006/0111669 A1   May 25, 2006

(51) Int. Cl.
*A61M 5/00* (2006.01)
*A61M 5/31* (2006.01)

(52) U.S. Cl. .................... 604/110; 604/194

(58) Field of Classification Search ............. 604/110, 604/192–198, 263
See application file for complete search history.

(56) References Cited

U.S. PATENT DOCUMENTS

| | | | |
|---|---|---|---|
| 4,927,414 A * | 5/1990 | Kulli | 604/110 |
| 4,994,034 A * | 2/1991 | Botich et al. | 604/110 |
| 5,019,044 A * | 5/1991 | Tsao | 604/110 |
| 5,049,133 A * | 9/1991 | Villen Pascual | 604/110 |
| 5,084,018 A * | 1/1992 | Tsao | 604/110 |
| 5,114,410 A * | 5/1992 | Caralt Batlle | 604/195 |
| 5,125,898 A * | 6/1992 | Kaufhold et al. | 604/110 |
| 5,180,370 A * | 1/1993 | Gillespie | 604/110 |
| 5,201,710 A * | 4/1993 | Caselli | 604/110 |
| 5,211,629 A * | 5/1993 | Pressly et al. | 604/110 |
| 5,395,337 A * | 3/1995 | Clemens et al. | 604/110 |
| 5,407,431 A * | 4/1995 | Botich et al. | 604/110 |
| 5,578,011 A * | 11/1996 | Shaw | 604/110 |
| 5,769,822 A * | 6/1998 | McGary et al. | 604/110 |
| 5,984,898 A * | 11/1999 | Garvin | 604/195 |
| 6,086,568 A * | 7/2000 | Caizza | 604/218 |
| 6,221,052 B1 * | 4/2001 | Caizza et al. | 604/195 |
| 6,572,565 B2 * | 6/2003 | Daley et al. | 600/573 |
| 6,743,199 B2 * | 6/2004 | Shue et al. | 604/110 |
| 6,921,386 B2 * | 7/2005 | Shue et al. | 604/164.01 |
| 2002/0193736 A1 * | 12/2002 | Kiehne | 604/110 |
| 2004/0106903 A1 * | 6/2004 | Shue et al. | 604/168.01 |
| 2006/0111671 A1 * | 5/2006 | Klippenstein | 604/110 |
| 2006/0129096 A1 * | 6/2006 | Wright | 604/110 |
| 2007/0185447 A1 * | 8/2007 | Lu | 604/110 |

* cited by examiner

*Primary Examiner*—Andrew M Gilbert
(74) *Attorney, Agent, or Firm*—Rosenberg, Klein & Lee

(57) ABSTRACT

A safety hypodermic syringe includes a barrel, which has a tapered hollow connector disposed at the front side and holds a needle assembly, a hollow plunger inserted into the barrel, and a retainer, which is fastened to the front side of the hollow plunger to keep the hollow plunger in a vacuum status and forced into engagement with the tapered hollow connector after the service of the safety hypodermic syringe for enabling the needle assembly and the retainer to be sucked into the inside of the hollow plunger after breaking of the tapered hollow connector from the barrel.

1 Claim, 4 Drawing Sheets

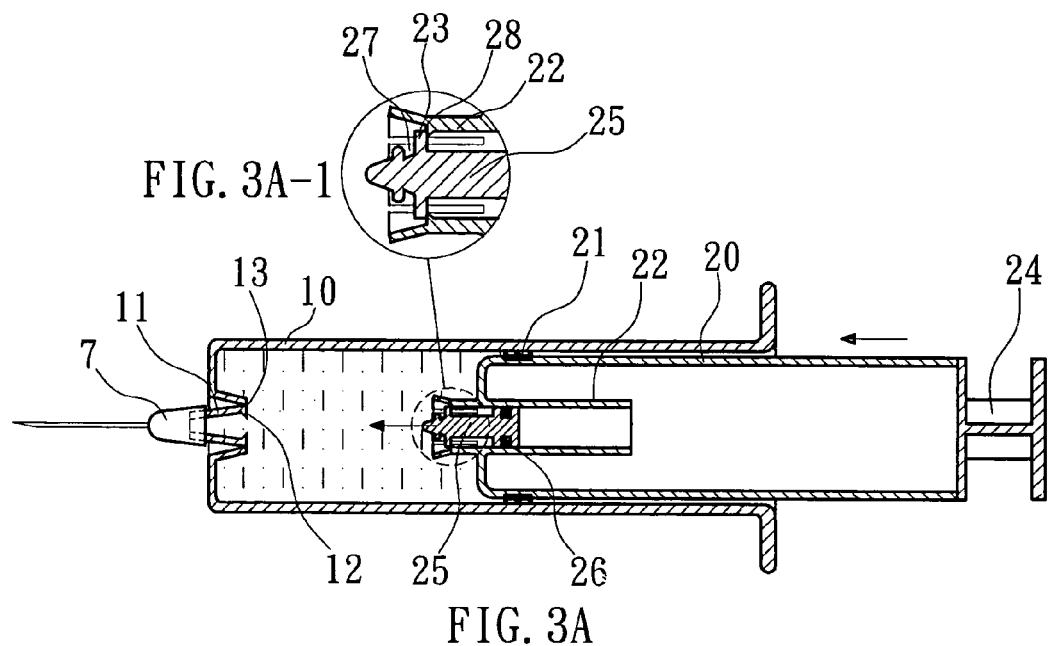
FIG. 3A-1
FIG. 3A
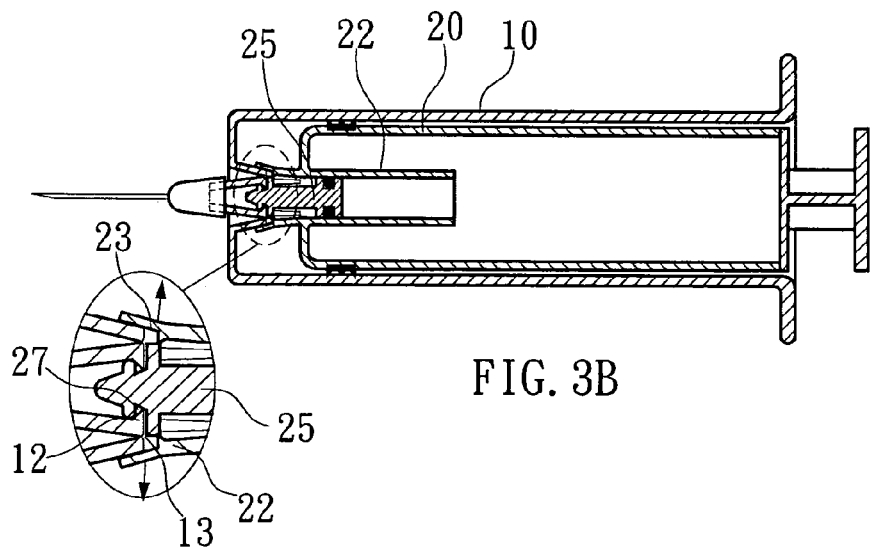
FIG. 3B
FIG. 3B-1
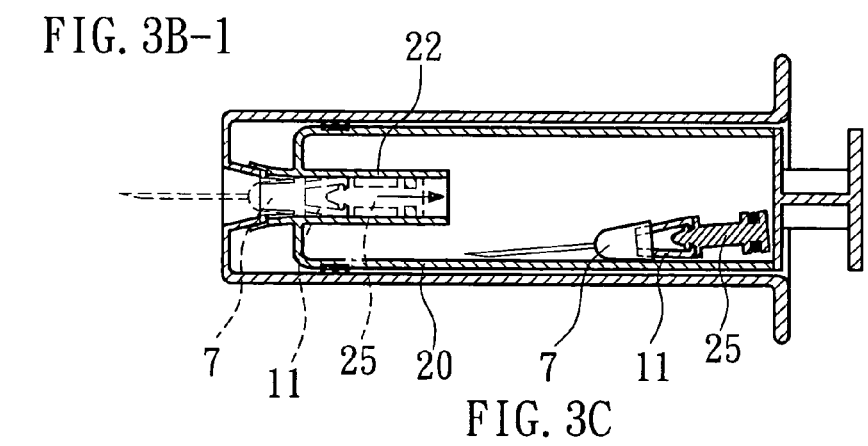
FIG. 3C

STRUCTURE OF SAFETY HYPODERMIC SYRINGE

BACKGROUND OF THE INVENTION

1. Field of the Invention

The present invention relates to a hypodermic syringe and more particularly, to a safety hypodermic syringe, which automatically receives the needle assembly inside the plunger by means of a vacuum to prevent contamination after the service of the safety hypodermic syringe.

2. Description of the Related Art

FIGS. 1A and 1B show the operation of a safety hypodermic syringe according to the prior art. According to this design, the safety hypodermic syringe comprises a barrel 1, which has a spring hook 2 extended from the outside wall and projecting into the inside, a hollow cylinder 3, which is inserted into the barrel 1 from the rear side and has a stop member 4 protruded from the periphery near the rear side, a needle assembly 7 fastened to the front side of the hollow cylinder 3 and extended out of the front side of the barrel 1, a tip protector 8 capped on the needle assembly 7, a plunger 6 inserted into the hollow cylinder 3 from the rear side, and a compression spring 5 mounted inside the barrel 1 and stopped between the front side of the barrel 1 and a part at the periphery of the hollow cylinder 3. After the service of the safety hypodermic syringe, the spring hook 2 is turned outwards and disengaged from the stop member 4, for enabling the compression spring 5 to push the hollow cylinder 3 backwards, and therefore the needle assembly 7 and the tip protector 8 are received with the hollow cylinder 3 inside the barrel 1. This structure of safety hypodermic syringe has numerous drawbacks as follows:

1. The compression spring 5 tends to be covered with rust if the safety hypodermic syringe is not used within a short period after its fabrication.
2. The spring hook 2 may be disengaged from the stop member 4 accidentally before the service of the safety hypodermic syringe; thereby causing the parts of the safety hypodermic syringe fall apart.
3. The safety hypodermic syringe is reusable after its service, and an evil person may recycle the used safety hypodermic syringe for a repeat use.
4. The complicated structure of the barrel 1 and hollow cylinder 3 greatly increases the manufacturing cost of the safety hypodermic syringe.

SUMMARY OF THE INVENTION

The present invention has been accomplished under the circumstances in view. It is the main object of the present invention to provide a safety hypodermic syringe, which automatically receives the needle assembly inside the plunger by means of a vacuum to prevent contamination after the service of the safety hypodermic syringe. It is another object of the present invention to provide a safety hypodermic syringe, which is inexpensive. To achieve these and other object of the present invention, the safety hypodermic syringe comprises a barrel, which has a tapered hollow connector disposed at the front side and holds a needle assembly, a hollow plunger inserted into the barrel, and a retainer, which is fastened to the front side of the hollow plunger to keep the hollow plunger in a vacuum status and forced into engagement with the tapered hollow connector after the service of the safety hypodermic syringe for enabling the needle assembly and the retainer to be sucked into the inside of the hollow plunger after breaking of the tapered hollow connector from the barrel.

BRIEF DESCRIPTION OF THE DRAWINGS

FIG. 3A is a schematic sectional view showing the operation of the safety hypodermic syringe according to the present invention (I).

FIG. 3A-1 is an enlarged view of a part of FIG. 3A.

FIG. 3B is a schematic sectional view showing the operation of the safety hypodermic syringe according to the present invention (II).

FIG. 3B-1 is an enlarged view of a part of FIG. 3B.

FIG. 3C is a schematic drawing showing the received status of the safety hypodermic syringe after the service according to the present invention.

DETAILED DESCRIPTION OF THE PREFERRED EMBODIMENT

Figure 1A:
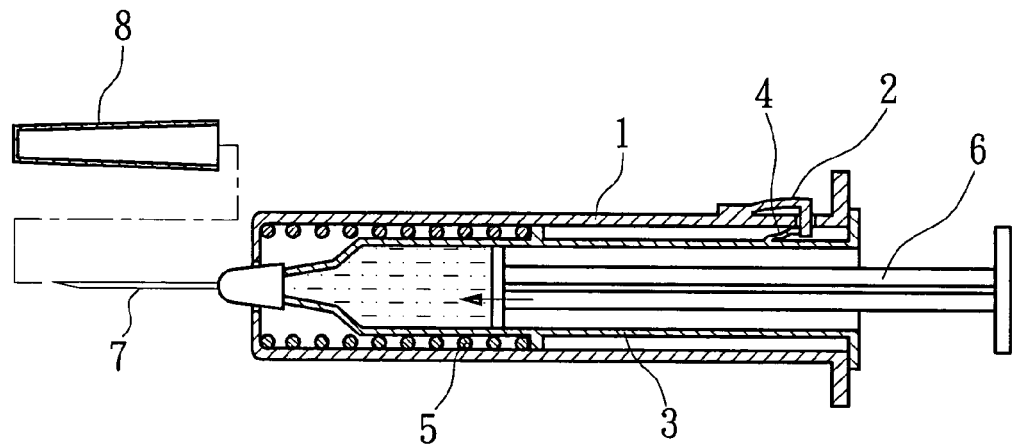
FIG. 1A is a schematic sectional view showing a prior art hypodermic syringe in operation.
Figure 1B:
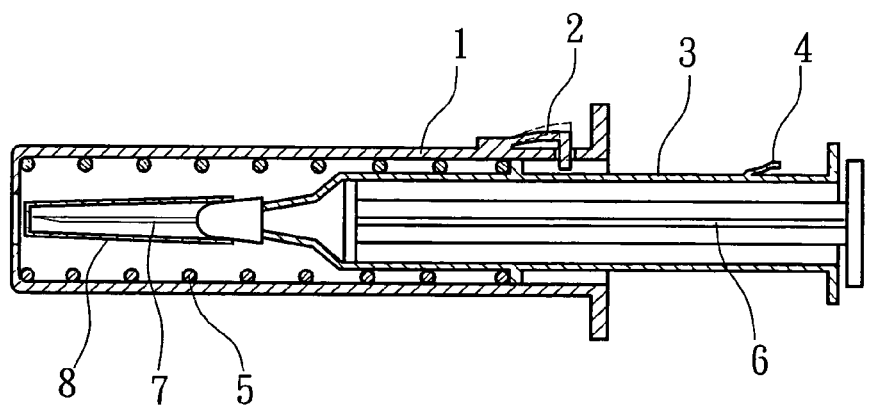
FIG. 1B is a schematic sectional view showing the prior art hypodermic syringe set in the received status after its service.
Figure 2:
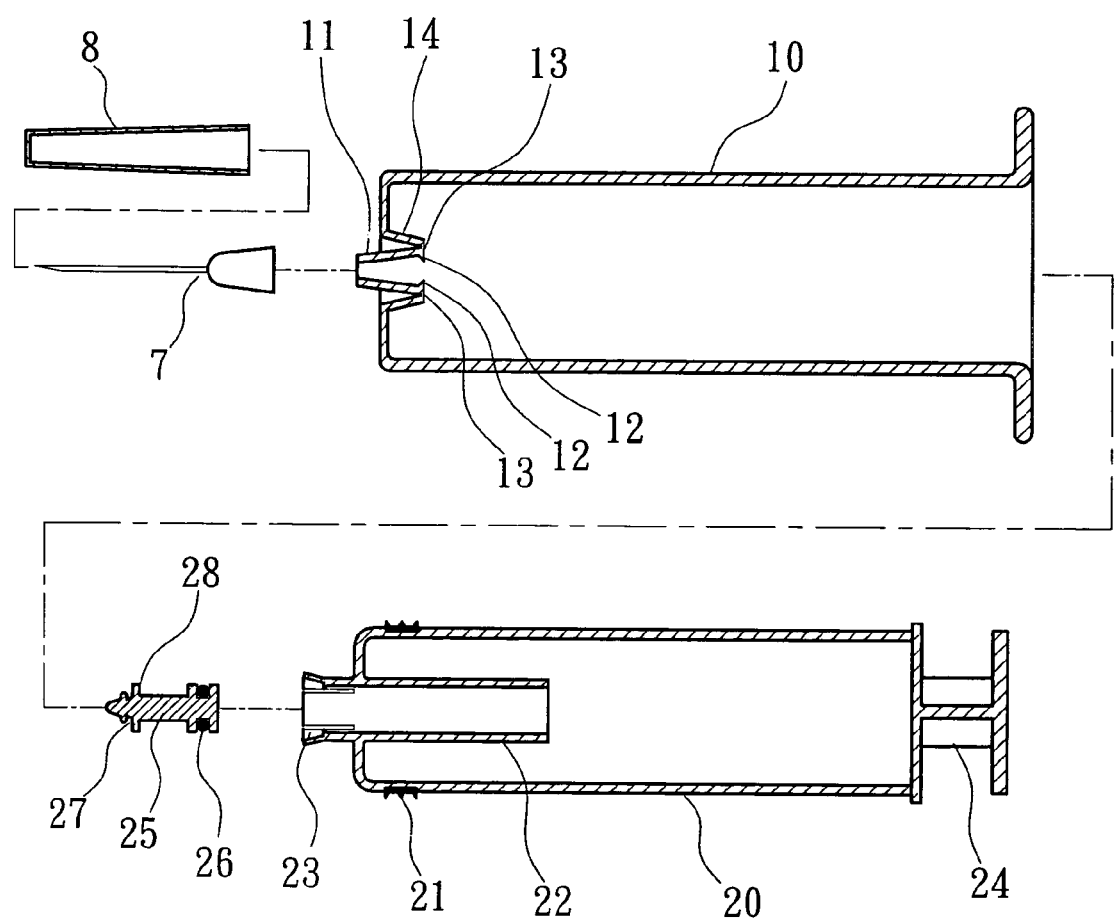
FIG. 2 is an exploded view in section of a safety hypodermic syringe according to the present invention.
Figure 4A:
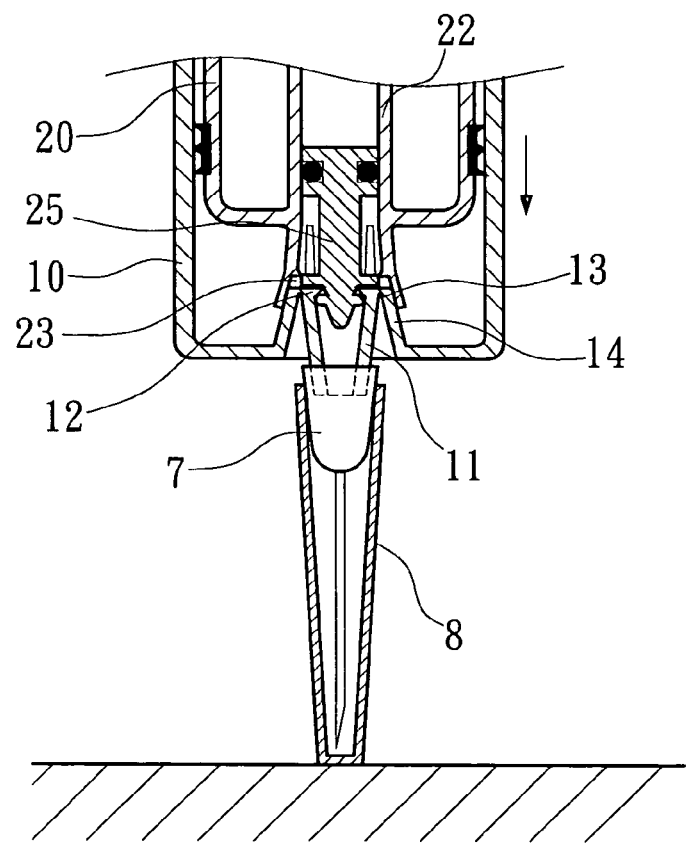
FIG. 4A is a schematic drawing showing the breakable thin connecting portion breaking operation according to the present invention (I).
Figure 4B:
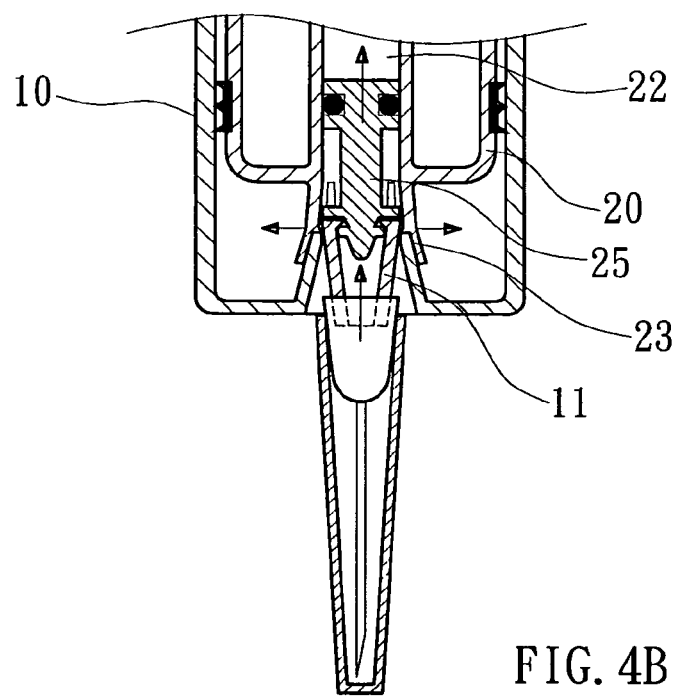
FIG. 4B is a schematic drawing showing the breakable thin connecting portion breaking operation according to the present invention (II).

Referring to FIGS. 2~4, a safety hypodermic syringe in accordance with the present invention is shown comprised of a barrel 10, a plunger 20, a retainer 25, a needle assembly 7, and a tip protector 8.

The barrel 1 comprises a tapered protruding portion 14 inwardly suspended at the center of the front side thereof, a tapered hollow connector 11 suspended in the tapered protruding portion 14, an annular flange 12 provided at the bottom (inner) side of the tapered protruding portion 14, and a breakable thin connecting portion 13 connected between the annular flange 12 and the tapered protruding portion 14.

The needle assembly 7 is fastened to the tapered hollow connector 11 outside the barrel 10.

The tip protector 8 is capped on the needle assembly 7 before service of the safety hypodermic syringe for protection.

The plunger 20 is a hollow cylindrical member axially slidably inserted into the barrel 10 and adapted to expel medicine out of the barrel 10 through the needle assembly 7. The plunger 20 comprises a grip 24 at the rear side, a seal ring 21 fastened to the periphery near the front side and disposed in close contact with the inside wall of the barrel 10, a center guide tube 22 axially disposed at the front side, and a front stop portion 23 provided around the periphery of the front end of the center guide tube 22.

The retainer 25 is fastened to the center guide tube 22 of the plunger 20, comprising a seal ring 26 fastened to the periphery near the rear end and disposed in close contact with the inside wall of the center guide tube 22, a stop flange 28 extended around the periphery near the front end, and a locating groove 27 extended around the periphery in front of the stop flange 28. After installation of the retainer 25 in the center guide tube 22 of the plunger 20, the plunger 20 is maintained in a vacuum status.

The operation of the safety hypodermic syringe is outlined hereinafter with reference to FIGS. 3 and 4 again. As shown in FIG. 3A, the stop flange 28 of the retainer 25 is stopped at the front side of the front stop portion 23 of the center guide tube 22 of the plunger 20, and therefore the vacuum in the plunger 20 cannot suck the retainer 25 to the inside of the plunger 20. After the plunger 20 has been pushed forwards to the front limit position to expel medicine out of the barrel 10 through the needle assembly 7 into the body of the patient, the locating groove 27 of the retainer 25 is forced into engagement with the annular flange 12 of the barrel 10. After the service of the safety hypodermic syringe, the tip protector 8 is capped on the needle assembly 7, and then the safety hypodermic syringe is turned upside down and pressed with the front tip of the tip protector 8 against the desk or a hard object to break the breakable thin connecting portion 13 and to expand the front stop portion 23 (see FIGS. 4A and 4B), for enabling the needle assembly 7 and the retainer 25 to be sucked into the inside of the barrel 20 by the vacuum in the barrel 20 (see FIG. 3C).

A prototype of safety hypodermic syringe has been constructed with the features of FIGS. 2~4. The safety hypodermic syringe functions smoothly to provide all the features discussed earlier.

Although a particular embodiment of the invention has been described in detail for purposes of illustration, various modifications and enhancements may be made without departing from the spirit and scope of the invention. Accordingly, the invention is not to be limited except as by the appended claims.

The invention claimed is:

1. A safety hypodermic syringe comprising:
   a barrel, said barrel comprising a tapered protruding portion inwardly suspended at the center of a front side thereof, a tapered hollow connector suspended in said tapered protruding portion and holding a needle assembly capped with a tip protector outside said barrel, an annular flange provided at an inner side of said tapered protruding portion, and a breakable thin connecting portion connected between said annular flange and said tapered protruding portion;
   a hollow cylindrical plunger axially slidably inserted into said barrel, said plunger comprising a rear grip, a seal ring fastened to the periphery near a front side thereof and disposed in close contact with an inside wall of said barrel, a center guide tube axially disposed at the front side, and a front stop portion provided around the periphery of a front end of said center guide tube; and
   a retainer fastened to said center guide tube of said plunger to hold said hollow cylindrical plunger in a vacuum status, said retainer comprising a seal ring fastened to the periphery near a rear end thereof and disposed in close contact with an inside wall of said center guide tube, a stop flange extended around the periphery near a front end thereof, and a locating groove extended around the periphery in front of said stop flange;
   wherein pushing said hollow cylindrical plunger forwards to the front side of said barrel causes said locating groove of said retainer to be forced into engagement with the annular flange of said tapered protruding portion; pressing said tip protector with said needle assembly and the safety hypodermic syringe against a hard object after the service of the safety hypodermic syringe causes said breakable thin connecting portion to be broken, for enabling said needle assembly and said retainer to be sucked into the inside of said hollow cylindrical plunger by the vacuum in said hollow cylindrical plunger.

* * * * *